(12) United States Patent
Liu et al.

(10) Patent No.: US 12,420,044 B2
(45) Date of Patent: Sep. 23, 2025

(54) RESPIRATOR AND VENTILATION CONTROL METHOD THEREFOR

(71) Applicants: SHENZHEN MINDRAY BIO-MEDICAL ELECTRONICS CO., LTD., Shenzhen (CN); ZHONGDA HOSPITAL SOUTHEAST UNIVERSITY, Nanjing (CN)

(72) Inventors: Ling Liu, Nanjing (CN); Jinglei Liu, Shenzhen (CN); Yi Yang, Nanjing (CN); Xiaoyong Zhou, Shenzhen (CN); Chun Pan, Nanjing (CN); Yongsheng Yan, Shenzhen (CN); Jianfeng Xie, Nanjing (CN); Songqiao Liu, Nanjing (CN); Haibo Qiu, Nanjing (CN)

(73) Assignees: SHENZHEN MINDRAY BIO-MEDICAL ELECTRONICS CO., LTD., Shenzhen (CN); ZHONGDA HOSPITAL SOUTHEAST UNIVERSITY, Nanjing (CN)

( * ) Notice: Subject to any disclaimer, the term of this patent is extended or adjusted under 35 U.S.C. 154(b) by 1038 days.

(21) Appl. No.: 17/086,544

(22) Filed: Nov. 2, 2020

(65) Prior Publication Data

US 2021/0093816 A1    Apr. 1, 2021

Related U.S. Application Data

(63) Continuation of application No. PCT/CN2018/085390, filed on May 2, 2018.

(51) Int. Cl.
*A61M 16/00* (2006.01)

(52) U.S. Cl.
CPC ...... *A61M 16/026* (2017.08); *A61M 16/0057* (2013.01); *A61M 2016/0027* (2013.01);
(Continued)

(58) Field of Classification Search
CPC ........ A61M 16/022; A61M 2016/0027; A61M 2016/003; A61M 2016/0036
See application file for complete search history.

(56) References Cited

U.S. PATENT DOCUMENTS

| | | | |
|---|---|---|---|
| 6,357,438 B1 * | 3/2002 | Hansen | A61M 16/0051 607/42 |
| 6,588,423 B1 * | 7/2003 | Sinderby | A61B 5/392 128/204.26 |

(Continued)

FOREIGN PATENT DOCUMENTS

| | | |
|---|---|---|
| CN | 1733330 A | 2/2006 |
| CN | 1973766 A | 6/2007 |

(Continued)

OTHER PUBLICATIONS

Esophageal-directed pressure support ventilation in normal volunteers. Barnard et al.; Chest 1999; 115; 482-489 (Year: 1999).*

(Continued)

*Primary Examiner* — Kathryn E Ditmer
(74) *Attorney, Agent, or Firm* — Morgan, Lewis & Bockius LLP

(57) ABSTRACT

The disclosure provides a respirator, which includes a ventilation device, configured for providing ventilation airflow to a patient. The respirator further includes a first monitor, configured for monitoring a pressure or a flow velocity with which the ventilation device ventilates the patient, and a second monitor, configured for measuring a pressure change that reflects a self-respiratory effort of the patient. The respirator also includes a processor, configured for identi- (Continued)

fying an inspiratory trigger moment or an expiratory trigger moment of the patient according to the pressure change that reflects the self-respiratory effort of the patient.

10 Claims, 6 Drawing Sheets

(52) U.S. Cl.
CPC ................ *A61M 2016/003* (2013.01); *A61M 2205/3344* (2013.01); *A61M 2205/50* (2013.01); *A61M 2210/105* (2013.01)

(56) References Cited

U.S. PATENT DOCUMENTS

| | | | |
|---|---|---|---|
| 9,027,552 B2 | 5/2015 | Angelico et al. | |
| 2002/0053345 A1* | 5/2002 | Jafari | A61M 16/205 128/204.23 |
| 2003/0000526 A1* | 1/2003 | Gobel | A61M 16/044 128/204.18 |
| 2003/0010339 A1* | 1/2003 | Banner | A61M 16/026 128/204.18 |
| 2003/0101998 A1* | 6/2003 | Zocca | A61M 16/044 128/207.15 |
| 2007/0113851 A1 | 5/2007 | Delisle et al. | |
| 2011/0100365 A1* | 5/2011 | Wedler | A61M 16/0057 128/204.23 |
| 2011/0273299 A1 | 11/2011 | Milne et al. | |
| 2011/0301481 A1* | 12/2011 | Heyer | A61M 16/021 600/529 |
| 2012/0125337 A1* | 5/2012 | Asanoi | A61M 16/026 128/204.23 |
| 2012/0152250 A1* | 6/2012 | Eger | A61M 16/0051 128/204.23 |
| 2013/0284172 A1* | 10/2013 | Doyle | A61M 16/0051 128/204.23 |
| 2014/0012150 A1* | 1/2014 | Milne | A61M 16/0051 600/529 |
| 2014/0048070 A1 | 2/2014 | Wedler et al. | |
| 2014/0116439 A1* | 5/2014 | Troili | A61M 16/0057 128/204.23 |
| 2014/0373845 A1* | 12/2014 | Dong | A61M 16/026 128/204.23 |
| 2015/0090258 A1* | 4/2015 | Milne | A61M 16/0051 128/204.23 |
| 2016/0045161 A1* | 2/2016 | Alshaer | A61B 5/097 600/538 |
| 2016/0045694 A1* | 2/2016 | Esmaeil-zadeh-azar | A61B 5/7239 128/204.23 |
| 2016/0058964 A1* | 3/2016 | Doemer | A61B 5/7264 128/204.23 |
| 2016/0114115 A1* | 4/2016 | Glenn | A61M 16/026 128/204.23 |
| 2016/0310730 A1* | 10/2016 | Martins | A61N 1/36031 |
| 2018/0177963 A1* | 6/2018 | Wang | A61B 5/085 |
| 2018/0193578 A1* | 7/2018 | Glenn | G16H 40/63 |
| 2018/0344194 A1* | 12/2018 | Eger | A61B 5/4836 |
| 2019/0000350 A1* | 1/2019 | Narayan | G16H 50/50 |
| 2019/0231202 A1* | 8/2019 | Kremeier | A61M 16/024 |

FOREIGN PATENT DOCUMENTS

| | | | | |
|---|---|---|---|---|
| CN | 101484202 A | 7/2009 | | |
| CN | 103340630 A | 10/2013 | | |
| CN | 104042439 A | 9/2014 | | |
| CN | 104135925 A | 11/2014 | | |
| CN | 105664313 A | 6/2016 | | |
| DE | 10213905 A1 | 10/2002 | | |
| WO | WO-0045881 A1 * | 8/2000 | ............ | A61M 16/00 |
| WO | WO-2009039527 A2 * | 3/2009 | ............ | A61M 16/00 |

OTHER PUBLICATIONS

Extended European Search Report issued in related European Application No. 18917420.4, mailed Apr. 13, 2021, 11 pages.
International Search Report issued in corresponding International Application No. PCT/CN2018/085390, mailed Feb. 2, 2019, 4 pages.
First Office issued in related Chinese Application No. 201880006528.6, mailed Dec. 3, 2021, 9 pages.
European Communication issued in related European Application No. 18917420.4, mailed Feb. 17, 2022, 9 pages.
Magdy Youne et al: "A method for monitoring and improving patient: ventilator interaction", Intensive Care Medicine, Springer, Berlin, DE, vol. 33, No. 8, May 31, 2007 (May 31, 2007), pp. 1337-1346, XP019536326, ISSN: 1432-1238, DOI: 10. 1007/S00134-007-0681-4.

* cited by examiner

RESPIRATOR AND VENTILATION CONTROL METHOD THEREFOR

CROSS-REFERENCE TO RELATED APPLICATION

This application is a bypass continuation of Patent Cooperation Treaty Application No. PCT/CN2018/085390, filed on May 2, 2018, the content thereof is hereby incorporated by reference in its entirety.

TECHNICAL FIELD

The present disclosure generally relates to the technical field of medical instruments, and specifically to a respirator and a ventilation control method for a respirator.

BACKGROUND ART

In modern clinical medicine, as an effective method that can artificially replace an autonomous ventilation function, respirators are widely applied to respiratory failure from various causes, respiration management in anesthesia during major surgery, respiratory support therapy, and emergency resuscitation. Respirators play a very important role in the field of modern medicine. As one of the key performance indicators of respirators, patient-respirator synchronization has drawn people's close attention.

Patient-respirator synchronization is the synchronization of a respiratory period of a respirator and the respiratory period of a patient. The respiratory period usually comprises four stages: inspiratory trigger, an inspiratory process, expiratory switching, and an expiratory process. Whether the respiratory period of the respirator is synchronous with the respiratory period of the patient is usually determined through comparison of whether inspiratory trigger of the respirator is synchronous with inspiratory trigger of the patient and whether expiratory switching of the respirator is synchronous with expiratory switching of the patient. The asynchrony of the patient and the respirator may lead to problems such as unstable respiration of the patient and patient-respirator conflict, and the conditions of the patient may be adversely affected.

At present, a respirator basically uses externally measured air passage pressure or air passage flow velocity to determine the inspiratory trigger or expiratory switching of the patient. For example, to determine inspiratory trigger, inspiratory trigger of the patient is determined when the air passage pressure is lower than PEEP-pressure trigger sensitivity, or inspiratory trigger of the patient is determined when the measured air passage flow velocity of the patient is greater than set flow velocity trigger sensitivity. To determine expiratory switching, the percentage of inspiratory peak flow velocity is generally used as a switching condition. For example, expiratory switching is determined when inspiratory flow velocity is less than 25% of inspiratory peak flow velocity.

However, the current method of determining inspiratory trigger or expiratory switching has the following problems: first, because respiratory effort of a patient is first reflected in the contraction of respiratory muscle and is then reflected at an air passage, the existing method of determining inspiratory trigger or expiratory switching of a patient by measuring the air passage pressure or air passage flow velocity has a delay between a signal measured by an in vitro sensor and actual trigger effort of the patient, and in this case, the patient needs to additionally do work to trigger inspiration or expiration, or the autonomous respiration strength of the patient fails to reach a trigger threshold and ineffective trigger occurs; and second, there is inevitable leakage at a gasbag responsible for airtightness in a conduit system, which causes inevitable leakage at a conduit system between a sensor in a respirator and an air passage of the patient, and the conduit system leads to an inaccurate in vitro monitoring signal due to leakage, as a result the respirator is prone to incorrect trigger or a trigger delay. In addition, the respirator is also prone to incorrect trigger or a trigger delay due to water accumulation in a conduit and vibration in a conduit.

SUMMARY

The present disclosure is designed in view of the foregoing cases, and a pressure change is used to control a ventilation mode of a respirator. The present disclosure can reduce a delay and avoid ineffective trigger, and can avoid a problem such as incorrect trigger or a trigger delay caused by a conduit system between a sensor in a respirator and an air passage of a patient.

For this, a first aspect of the present disclosure provides a respirator, comprising: a ventilation device, configured for providing ventilation airflow to a patient; a first monitor, configured for monitoring the pressure and/or flow velocity with which the ventilation device ventilates the patient; a second monitor, configured for measuring a pressure change that reflects the self-respiratory effort of the patient; and a processor, identifying an inspiratory trigger moment or an expiratory trigger moment of the patient according to the measured pressure change that reflects the self-respiratory effort of the patient.

In the present disclosure, the ventilation device provides ventilation airflow to a patient, the pressure and/or flow velocity of the ventilation is monitored by a first monitor, the second monitor monitors a pressure change that reflects the self-respiratory effort of the patient, and a processor identifies an inspiratory trigger moment or an expiratory trigger moment of the patient according to the pressure change. Therefore, a delay problem that occurs when the inspiratory trigger moment or expiratory trigger moment of the patient is determined according to air passage pressure or air passage flow velocity can be resolved. In addition, the pressure change that reflects the self-respiratory effort of the patient can avoid a leakage problem.

In the respirator according to the first aspect of the present disclosure, the processor identifies the inspiratory trigger moment or the expiratory trigger moment according to one or more of the speed, trend, and amplitude of the pressure change that reflects the self-respiratory effort. In this case, the inspiratory trigger moment or the expiratory trigger moment of the patient is accurately identified.

In the respirator according to the first aspect of the present disclosure, the pressure change comprises a pressure change in one or more of esophageal pressure, intrapulmonary pressure, carina pressure, intragastric pressure or cannula tip pressure of the patient. In this case, the inspiratory trigger moment or the expiratory trigger moment of the patient can be identified according to the pressure change in one or more of esophageal pressure, intrapulmonary pressure, carina pressure, intragastric pressure or cannula tip pressure.

In the respirator according to the first aspect of the present disclosure, after inspiratory trigger is identified, the ventilation device is controlled to switch from an expiratory phase to an inspiratory phase, and after expiratory trigger is identified, the ventilation device is controlled to switch from the inspiratory phase to the expiratory phase. In this case, expiration or inspiration of the patient can be facilitated.

In the respirator according to the first aspect of the present disclosure, after inspiratory trigger and expiratory trigger are identified, the inspiratory trigger moment and the expiratory trigger moment are output. In this case, the inspiratory trigger moment and the expiratory trigger moment of the patient can be read.

In the respirator according to the first aspect of the present disclosure, after inspiratory trigger and expiratory trigger are identified, patient-respirator synchronization information is computed. In this case, patient-respirator synchronization of the respirator can be determined.

In the respirator according to the first aspect of the present disclosure, the second monitor obtains the amplitude of the pressure change and the trend of the pressure change, and the processor identifies, when the pressure change is in a downward trend and the amplitude of the pressure change reaches a first threshold, that the patient is at the inspiratory trigger moment, and identifies, when the pressure change is in an upward trend and the amplitude of the pressure change reaches a second threshold, that the patient is at the expiratory trigger moment. In this case, the inspiratory trigger moment or expiratory trigger moment of the patient can be accurately identified.

In the respirator according to the first aspect of the present disclosure, the amplitude of the pressure change is a difference value between pressure measured by the second monitor and end-tidal pressure. In this case, the inspiratory trigger moment or expiratory trigger moment of the patient can be identified based on the amplitude of the pressure change.

In the respirator according to the first aspect of the present disclosure, the first threshold and the second threshold both are constant thresholds or variable thresholds. In this case, thresholds can be set or adjusted according to the experience of medical personnel. The respirator can also automatically adjust thresholds according to historical data (for example, machine learning).

In the respirator according to the first aspect of the present disclosure, the second monitor obtains the speed of the pressure change, and the processor identifies, when the speed of the pressure change decreases from near zero, that the patient is at the inspiratory trigger moment, and identifies, when the speed of the pressure change decreases to near zero, that the patient is at the expiratory trigger moment. In this case, the inspiratory trigger moment or expiratory trigger moment of the patient can be accurately identified.

In the respirator according to the first aspect of the present disclosure, the amplitude of the pressure change is a change amplitude of an actually measured pressure and a predicted pressure, and the first threshold and the second threshold are both greater than zero. In this case, the inspiratory trigger moment or expiratory trigger moment of the patient can be identified based on the amplitude of the pressure change.

In the respirator according to the first aspect of the present disclosure, the predicted pressure is obtained by performing fitting prediction on the actually measured pressure. In this case, the predicted pressure can be obtained.

In the respirator according to the first aspect of the present disclosure, the second monitor obtains a pressure waveform that reflects the self-respiratory effort of the patient, and the processor extracts an envelope from the pressure waveform, and identifies the inspiratory trigger moment or the expiratory trigger moment of the patient according to the envelope. In this case, the inspiratory trigger moment of expiratory trigger moment of the patient can be accurately identified based on the envelope.

In the respirator according to the first aspect of the present disclosure, the identifying the inspiratory trigger moment or the expiratory trigger moment of the patient according to the envelope is specifically: identifying the inspiratory trigger moment and the expiratory trigger moment of the patient according to a peak and a trough of the envelope. In this case, the inspiratory trigger moment and the expiratory trigger moment of the patient can be identified based on the peak and the trough of the envelope.

A second aspect of the present disclosure provides a ventilation control method for a respirator, comprising: providing ventilation airflow to a patient by using a ventilation device; monitoring the pressure and/or flow velocity of ventilation provided by the ventilation device to the patient; measuring a pressure change that reflects the self-respiratory effort of the patient; and identifying an inspiratory trigger moment or an expiratory trigger moment of the patient according to the measured pressure change that reflects the self-respiratory effort of the patient.

In the present disclosure, ventilation airflow is provided to a patient by using the ventilation device, the pressure and/or flow velocity of the ventilation is monitored, a pressure change that reflects the self-respiratory effort of the patient is measured, and an inspiratory trigger moment or an expiratory trigger moment of the patient is identified according to the pressure change. Therefore, a delay problem that occurs when the inspiratory trigger moment or expiratory trigger moment of the patient is determined according to air passage pressure or air passage flow velocity can be resolved. In addition, the pressure change that reflects the self-respiratory effort of the patient can avoid a leakage problem.

In the ventilation control method for a respirator according to the second aspect of the present disclosure, the inspiratory trigger moment or the expiratory trigger moment is identified according to one or more of the speed, trend, and amplitude of the pressure change that reflects the self-respiratory effort. In this case, the inspiratory trigger moment or the expiratory trigger moment of the patient is accurately identified.

In the ventilation control method for a respirator according to the second aspect of the present disclosure, the pressure change comprises a pressure change in one or more of esophageal pressure, intrapulmonary pressure, carina pressure, intragastric pressure or cannula tip pressure of the patient. In this case, the inspiratory trigger moment or the expiratory trigger moment of the patient can be identified according to the pressure change in one or more of esophageal pressure, intrapulmonary pressure, carina pressure, intragastric pressure or cannula tip pressure.

In the ventilation control method for a respirator according to the second aspect of the present disclosure, after the inspiratory trigger moment is identified, the ventilation device is controlled to switch from an expiratory phase to an inspiratory phase, and after the expiratory trigger moment is identified, the ventilation device is controlled to switch from the inspiratory phase to the expiratory phase. In this case, expiration or inspiration of the patient can be facilitated.

In the ventilation control method for a respirator according to the second aspect of the present disclosure, after the inspiratory trigger moment and the expiratory trigger moment are identified, the ventilation control method further comprises: outputting the inspiratory trigger moment and the expiratory trigger moment. In this case, the inspiratory trigger moment and the expiratory trigger moment of the patient can be identified.

In the ventilation control method for a respirator according to the second aspect of the present disclosure, after the inspiratory trigger moment and the expiratory trigger moment are identified, the ventilation control method further comprises: computing patient-respirator synchronization information. In this case, patient-respirator synchronization of the respirator can be determined.

In the ventilation control method for a respirator according to the second aspect of the present disclosure, the pressure change that reflects the self-respiratory effort of the patient is the amplitude and trend of the pressure change; and the identifying an inspiratory trigger moment or an expiratory trigger moment of the patient according to the measured pressure change that reflects the self-respiratory effort of the patient is specifically: identifying, when the pressure change is in a downward trend and the amplitude of the pressure change reaches a first threshold, that the patient is at the inspiratory trigger moment, and identifying, when the pressure change is in an upward trend and the amplitude of the pressure change reaches a second threshold, that the patient is at the expiratory trigger moment. In this case, the inspiratory trigger moment or expiratory trigger moment of the patient can be accurately identified.

In the ventilation control method for a respirator according to the second aspect of the present disclosure, the amplitude of the pressure change is a change amplitude of an actually measured pressure and end-tidal pressure. In this case, the inspiratory trigger moment or expiratory trigger moment of the patient can be identified based on the amplitude of the pressure change.

In the ventilation control method for a respirator according to the second aspect of the present disclosure, the first threshold and the second threshold both are constant thresholds or variable thresholds. In this case, thresholds can be set or adjusted according to the experience of medical personnel.

In the ventilation control method for a respirator according to the second aspect of the present disclosure, the pressure change that reflects the self-respiratory effort of the patient is the speed of the pressure change; and the identifying an inspiratory trigger moment or an expiratory trigger moment of the patient according to the measured pressure change that reflects the self-respiratory effort of the patient is specifically: identifying, when the speed of the pressure change decreases from near zero, that the patient is at the inspiratory trigger moment, and identifying, when the speed of the pressure change decreases to near zero, that the patient is at the expiratory trigger moment. In this case, the inspiratory trigger moment or expiratory trigger moment of the patient can be accurately identified.

In the ventilation control method for a respirator according to the second aspect of the present disclosure, the amplitude of the pressure change is a change amplitude of an actually measured pressure and a predicted pressure, and the first threshold and the second threshold are both greater than zero. In this case, the inspiratory trigger moment or expiratory trigger moment of the patient can be identified based on the amplitude of the pressure change.

In the ventilation control method for a respirator according to the second aspect of the present disclosure, the predicted pressure is obtained by performing fitting prediction on the actually measured pressure. In this case, the predicted pressure can be obtained.

In the ventilation control method for a respirator according to the second aspect of the present disclosure, the measuring a pressure change that reflects the self-respiratory effort of the patient is specifically: obtaining a pressure waveform that reflects the self-respiratory effort of the patient, and extracting an envelope from the pressure waveform; and the identifying an inspiratory trigger moment or an expiratory trigger moment of the patient according to the measured pressure change that reflects the self-respiratory effort of the patient is specifically: identifying the inspiratory trigger moment or the expiratory trigger moment of the patient according to the envelope. In this case, the inspiratory trigger moment or expiratory trigger moment of the patient can be accurately identified based on the envelope.

In the ventilation control method for a respirator according to the second aspect of the present disclosure, the identifying the inspiratory trigger moment or the expiratory trigger moment of the patient according to the envelope is specifically: identifying the inspiratory trigger moment and the expiratory trigger moment of the patient according to a peak and a trough of the envelope. In this case, the inspiratory trigger moment and the expiratory trigger moment of the patient can be identified based on the peak and the trough of the envelope.

By means of the respirator provided in the disclosure, the ventilation synchronization of the respirator can be improved, thereby reducing delays in inspiratory and expiratory trigger, avoiding ineffective trigger, and avoiding incorrect respiratory trigger or a trigger delay due to leakage, water accumulation, vibration, and the like in a respiratory conduit system.

BRIEF DESCRIPTION OF THE DRAWINGS

The embodiments of the present disclosure are now further described in detail merely with reference to the examples in the accompanying drawings, in which.

DETAILED DESCRIPTION OF EMBODIMENTS

Figure 1:
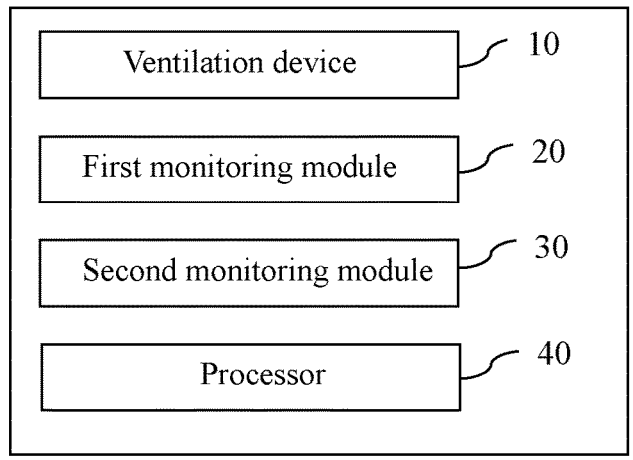
FIG. 1 is a schematic structural diagram of a respirator according to the present disclosure.

The preferred embodiments of the present disclosure are described below in detail with reference to the accompanying drawings. In the following description, the same components are provided with the same reference numerals. Repeated description is omitted. In addition, the accompanying drawings are schematic figures. The proportions among the sizes of the components, the shapes of the components, and the like may be different from those in reality.

It needs to be noted that the terms "comprise" and "have" or any variation of such terms in the present disclosure are intended to cover a non-exclusive inclusion. For example, a process, method, system, product or device that includes a series of steps or units not only includes those steps or units specified expressly, but also includes other steps or units that are not specified expressly or are inherent to the process, method, product or device. A person skilled in the art should be aware of many methods and materials similar to or equivalent to those that are in the practice of the present disclosure and are described in the present disclosure. In fact, the present disclosure is not limited to the described methods and materials.

In addition, the subtitles mentioned in the following description of the present disclosure are not intended to limit the content or scope of the present disclosure, and are merely used as prompts for reading. Such subtitles should not be construed as dividing the content of the article, and the content under the subtitles should not be limited to the scope of the subtitles. Unless otherwise defined, the technical terms and scientific terms used in the present disclosure have the same meaning as how they are generally understood by those of ordinary skill in the art to which the present disclosure pertains.

The present disclosure provides a respirator 1. FIG. 1 is a schematic structural diagram of a respirator according to the present disclosure.

In some examples, as shown in FIG. 1, the respirator 1 may comprise a ventilation device 10, a first monitor 20, a second monitor 30, and a processor 40.

In some examples, the ventilation device 10 may provide ventilation airflow to a patient. That is, the ventilation device 10 ventilates the patient to facilitate the respiration of the patient.

In some examples, the ventilation device 10 may have an inspiratory phase for providing inhalation gas to the patient and an expiratory phase for facilitating expiration of the patient. That is, the ventilation device 10 may facilitate inspiration of the patient or facilitate expiration of the patient.

In some examples, inhalation gas provided by the ventilation device 10 to the patient may be oxygen or may be mixed gas of air and oxygen. However, an example in the present disclosure is not limited thereto. The inhalation gas may be alternatively mixed gas of helium and oxygen. The inhalation gas may be, for example, compressed gas provided by a central gas supply system in a hospital or may be gas from the environment.

In some examples, the ventilation device 10 may further comprise a flow regulation device. The flow regulation device may implement control of the air pressure and/or flow velocity of the ventilation airflow.

In some examples, as shown in FIG. 1, the respirator 1 may further comprise the first monitor 20. The first monitor 20 may monitor the pressure and/or flow velocity with which the ventilation device 10 ventilates the patient.

In some other examples, the first monitor 20 may measure at least one of air passage pressure or air passage flow velocity of the patient.

In some examples, the first monitor 20 may comprise at least one of a pressure sensor and a flow sensor. The pressure sensor in the first monitor 20 may monitor the pressure with which the ventilation device 10 ventilates the patient or the air passage pressure of the patient. The flow sensor may monitor the flow velocity or air passage flow velocity with which the ventilation device 10 ventilates the patient.

In some examples, as shown in FIG. 1, the respirator 1 may further comprise the second monitor 30. The second monitor 30 may measure a pressure change that reflects the self-respiratory effort of the patient. The processor 40 may identify an inspiratory trigger moment or an expiratory trigger moment of the patient according to the measured pressure change that reflects the self-respiratory effort of the patient.

In some examples, the pressure change may comprise a pressure change in one or more of esophageal pressure, thoracic cavity pressure, intrapulmonary pressure, carina pressure, intragastric pressure or cannula tip pressure of the patient. Specifically, the second monitor 30 may choose to measure at least one of esophageal pressure, thoracic cavity pressure, intrapulmonary pressure, carina pressure, intragastric pressure or cannula tip pressure of the patient. In some examples, the second monitor 30 may comprise a pressure sampling tube. The pressure sampling tube may be at least one of an esophageal pressure sampling tube, a thoracic cavity pressure sampling tube, and a carina pressure sampling tube. The esophageal pressure sampling tube may be inserted into the esophagus of the patient to acquire esophageal pressure. The thoracic cavity pressure sampling tube may be inserted into the pleural cavity of the patient to acquire thoracic cavity pressure. The carina pressure sampling tube may be inserted into a carina of the patient to acquire carina pressure. The processor 40 can identify the inspiratory trigger moment or the expiratory trigger moment of the patient according to the pressure change in one or more of esophageal pressure, thoracic cavity pressure, intrapulmonary pressure, carina pressure, intragastric pressure or cannula tip pressure.

In some examples, the processor 40 may identify the inspiratory trigger moment or the expiratory trigger moment according to one or more of the speed, trend, and amplitude of the pressure change that reflects the self-respiratory effort. In this case, the inspiratory trigger moment or the expiratory trigger moment of the patient is accurately identified.

The speed of the pressure change may be the speed at which the value of the pressure change increases or decreases. The trend of the pressure change may be a change trend of pressure. The amplitude of the pressure change may be the value of the pressure change. The value of the pressure change may be sometimes referred to as a difference value of pressure.

In some examples, the processor 40 may obtain the amplitude of the pressure change and the trend of the pressure change. The amplitude of the pressure change may be a difference value between the pressure measured by the second monitor 30 and end-tidal pressure. The end-tidal pressure used to calculate the amplitude of the pressure change may be the end-tidal pressure within a previous respiratory period or may be an average value of end-tidal pressure of a set quantity of previous respiratory periods, or may be an empirical value that is set by medical personnel according to experience and stored in the respirator.

The speed of the pressure change may be the slope of the pressure measured by the second monitor 30, or may be sometimes referred to as a pressure gradient value.

The pressure measured by the second monitor 30 may be a discrete signal. The processor 40 may perform differential operation on the pressure obtained by the second monitor 30 to acquire the speed of the pressure change. Certainly, the speed of the pressure change may be obtained by performing linear fitting on instantaneous pressure obtained by the second monitor 30 within a preset time to calculate the slope of the instantaneous pressure. The preset time may be 200 ms to 600 ms.

In some other examples, the processor 40 may obtain the amplitude of the pressure change and the trend of the pressure change. The amplitude of the pressure change may be a change amplitude of an actually measured pressure measured by the second monitor 30 and a predicted pressure, that is, the magnitude of a difference value between the actually measured pressure and the predicted pressure.

In some examples, the predicted pressure may perform fitting prediction on the actually measured pressure to obtain the predicted pressure.

In some examples, the fitting prediction is a process of establishing a model based on at least two sampling points to approximate an actual data sequence.

In some examples, the processor 40 identifies, when the pressure change measured by the second monitor 30 is in a downward trend and the amplitude of the pressure change reaches a first threshold, that the patient is at the inspiratory trigger moment, and identifies, when the pressure change measured by the second monitor 30 is in an upward trend and the amplitude of the pressure change reaches a second threshold, that the patient is at the expiratory trigger moment. In this case, the inspiratory trigger moment or expiratory trigger moment of the patient can be accurately identified based on the amplitude and trend of the pressure change.

In some examples, the first threshold and the second threshold both are constant thresholds or variable thresholds. In this case, thresholds can be set or adjusted according to the experience of medical personnel. The constant thresholds are unchangeable thresholds set in the respirator. The variable thresholds are thresholds that are set in the respirator and can be manually changed. In this case, the first threshold and the second threshold may be set or adjusted according to experience of medical personnel. Certainly, the first threshold and the second threshold may be alternatively obtained by the machine through learning of historical data.

In some examples, the processor 40 identifies, when the speed of the pressure change measured by the second monitor 30 decreases from near zero, that the patient is at the inspiratory trigger moment, and identifies, when the speed of the measured pressure change decreases to near zero, that the patient is at the expiratory trigger moment. That is, when the pressure gradient value crosses zero and gradually decreases, it is identified that the patient is at the inspiratory trigger moment. When the pressure gradient value decreases to zero, it is identified that the patient is at the expiratory trigger moment. In this case, the inspiratory trigger moment or expiratory trigger moment of the patient can be accurately identified.

In some examples, the processor 40 identifies the inspiratory trigger moment and expiratory trigger moment according to the amplitude of the pressure change and the trend of the pressure change obtained by the second monitor 30. Specifically, the processor 40 identifies, when the pressure change measured by the second monitor 30 is in a downward trend and the amplitude of the pressure change reaches the first threshold, that the patient is at the inspiratory trigger moment, and identifies, when the measured pressure change is in an upward trend and the amplitude of the pressure change reaches the second threshold, that the patient is at the expiratory trigger moment. In this case, the inspiratory trigger moment or expiratory trigger moment of the patient can be accurately identified based on the amplitude and trend of the pressure change.

In some other examples, the processor 40 extracts an envelope from a pressure waveform measured by the second monitor 30, and identifies the inspiratory trigger moment or the expiratory trigger moment of the patient according to the envelope. In this case, the inspiratory trigger moment or expiratory trigger moment of the patient can be accurately identified based on the envelope.

In some examples, the pressure waveform may comprise an interference signal such as heartbeat-caused pressure fluctuations. The processor 40 may perform filtering processing on the pressure waveform, to filter out an interference signal such as heartbeat.

In some examples, the identifying the inspiratory trigger moment or the expiratory trigger moment of the patient according to the envelope is specifically: identifying the inspiratory trigger moment and the expiratory trigger moment of the patient according to a peak and a trough of the envelope. In this case, the inspiratory trigger moment and the expiratory trigger moment of the patient can be identified based on the peak and the trough of the envelope.

In some examples, when the pressure waveform is at a peak, the processor 40 identifies the inspiratory trigger moment of the patient, and when the pressure waveform is at a trough, the processor 40 identifies the expiratory trigger moment of the patient.

In some examples, the inspiratory trigger moment does not necessarily correspond to a peak of the pressure waveform, and the moment when the pressure waveform rises or drops to a first set proportion of the peak may be considered as the inspiratory trigger moment, or a first set time at a delay after the moment corresponding to a peak may be considered as the inspiratory trigger moment.

Similarly, the expiratory trigger moment does not necessarily correspond to a peak of the pressure waveform, and the moment when the pressure waveform drops or rises to a second set proportion of a trough may be considered as the expiratory trigger moment, or a second set time at a delay after the moment corresponding to a trough may be considered as the expiratory trigger moment.

In some examples, the processor 40 may further control, after the inspiratory trigger moment is identified, the ventilation device 10 to switch from an expiratory phase to an inspiratory phase, or control, after the expiratory trigger moment is identified, the ventilation device 10 to switch from the inspiratory phase to the expiratory phase. In this case, expiration or inspiration of the patient can be facilitated.

In some examples, after the inspiratory trigger moment and the expiratory trigger moment are identified, the processor 40 may compute patient-respirator synchronization information. In this case, patient-respirator synchronization of the respirator can be determined. A method for determining patient-respirator synchronization is described below in detail.

In some examples, the respirator 1 may further comprise a display module (not shown in the figure). The processor 40 outputs the inspiratory trigger moment and the expiratory trigger moment after the inspiratory trigger moment and the expiratory trigger moment are identified, and displays the inspiratory trigger moment and the expiratory trigger moment on the display module. In this case, the inspiratory trigger moment and the expiratory trigger moment of the patient can be read.

In the present disclosure, the ventilation device 10 provides ventilation airflow to a patient. The pressure and/or flow velocity of ventilation is monitored by the first monitor 20. The second monitor 30 monitors a pressure change that reflects the self-respiratory effort of the patient. The processor 40 may identify an inspiratory trigger moment or the expiratory trigger moment of the patient according to the pressure change. Therefore, a delay problem that occurs when the inspiratory trigger moment or expiratory trigger moment of the patient is determined according to air passage pressure or air passage flow velocity can be resolved. In addition, the pressure change that reflects the self-respiratory effort of the patient can avoid a leakage problem.

In some examples, the respirator 1 may further measure the air passage pressure and/or air passage flow velocity. When the air passage pressure is in a downward trend and/or the air passage flow velocity is in an upward trend, the processor 40 identifies that the patient is at the inspiratory trigger moment. When the air passage pressure is in an upward trend and/or the air passage flow velocity is in a downward trend, the processor 40 identifies that the patient is at the expiratory trigger moment. In addition, the processor 40 may control the air pressure and/or flow velocity in the inspiratory phase and the expiratory phase according to the air passage pressure and/or air passage flow velocity target. The air passage pressure and/or air passage flow velocity target may be a preset pressure value or flow velocity value.

In some examples, the respirator 1 may further measure both the air passage pressure and/or air passage flow velocity, and the pressure change that reflects the self-respiratory effort of the patient. The inspiratory trigger moment or the expiratory trigger moment of the patient is identified by determining the air passage pressure and/or air passage flow velocity and determining the pressure change that reflects the self-respiratory effort of the patient, to make ventilation switching of the respirator 1 more accurate.

The respirator according to the present disclosure is provided below. The ventilation control method according to the present disclosure is described below in detail with reference to a flowchart and a waveform diagram. The foregoing pressure change and the following pressure change are one same concept.

In an existing ventilation control method for a respirator, the air passage pressure or air passage flow velocity of a patient is usually measured to implement ventilation control of a respirator. However, in the ventilation control method according to the present disclosure for a respirator, a pressure change that reflects the self-respiratory effort of the patient is mainly measured, and an inspiratory trigger moment or an expiratory trigger moment of the patient is identified according to the measured pressure change that reflects the self-respiratory effort of the patient. A sampling position for measured pressure that reflects the self-respiratory effort of the patient is in the body of the patient, so that influence caused by a conduit leakage problem can be avoided.

Figure 2:
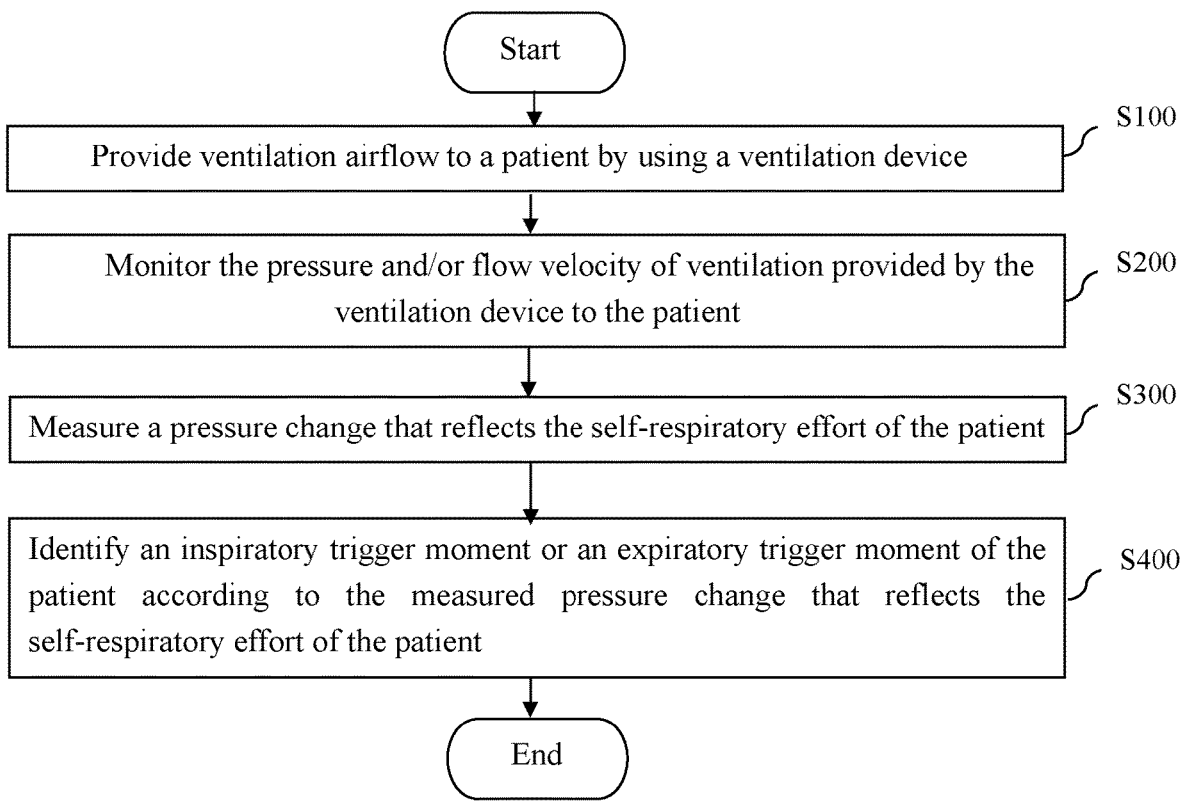
FIG. 2 is a schematic flowchart of a ventilation control method for a respirator according to the present disclosure.

The present disclosure provides a ventilation control method for a respirator. FIG. 2 is a schematic flowchart of a ventilation control method for a respirator according to the present disclosure.

In some examples, as shown in FIG. 1, the ventilation control method for a respirator comprises: providing ventilation airflow to a patient by using a ventilation device (step S100); monitoring the pressure and/or flow velocity of ventilation provided by the ventilation device to the patient (step S200); measuring a pressure change that reflects the self-respiratory effort of the patient (step S300); and identifying an inspiratory trigger moment or an expiratory trigger moment of the patient according to the measured pressure change that reflects the self-respiratory effort of the patient (step S400).

In some examples, in step S100, the ventilation device is used to provide ventilation to the patient. The ventilation device 10 may have an inspiratory phase for providing inhalation gas to the patient and an expiratory phase for facilitating expiration of the patient. For the ventilation device 10, reference may be made to the foregoing description of the respirator 1.

In some examples, the gas provided in the inspiratory phase may be oxygen or may be mixed gas of air and oxygen. However, an example in the present disclosure is not limited thereto. The inhalation gas may be alternatively mixed gas of helium and oxygen. The inhalation gas may be, for example, compressed gas provided by a central gas supply system in a hospital or may be gas from the environment.

In some examples, the ventilation control method for a respirator may comprise: monitoring the pressure and/or flow velocity of ventilation provided by the ventilation device to the patient (step S200).

However, an example in the present disclosure is not limited thereto, and in step S200, at least one of the air passage pressure or air passage flow velocity of the patient may further be measured.

In step S200, the pressure of the ventilation or the air passage pressure of the patient may be measured by the pressure sensor. The flow velocity of the provided ventilation or the air passage flow velocity of the patient may be measured by a flow sensor.

In some examples, as shown in FIG. 2, the ventilation control method for a respirator may further comprise: measuring a pressure change that reflects the self-respiratory effort of the patient (step S300).

In step S300, the pressure change may comprise a pressure change in one or more of esophageal pressure, thoracic cavity pressure, intrapulmonary pressure, carina pressure, intragastric pressure or cannula tip pressure of the patient. Therefore, because there is no airflow at the foregoing measured pressure (for example, esophageal pressure and thoracic cavity pressure), the problem such as incorrect trigger caused by leakage can be avoided.

The foregoing several pressure changes may reflect pressure changes at the muscle during the self-respiratory effort of the patient. An inspiratory instruction (or expiratory instruction) of the respiration of a human body is usually executed by the muscle first and is then reflected to an air passage. The longest time is consumed from the muscle to the air passage. Therefore, compared with the measurement of air passage pressure or air passage flow velocity, in the measurement of the foregoing pressure change, the longest time consumed in the foregoing path may be saved, so that a delay problem caused during measurement of air passage pressure or air passage flow velocity can be resolved to some extent.

In some examples, in step S300, the pressure sampling tube may be used to measure the pressure change that reflects the self-respiratory effort of the patient. The pressure sampling tube may be at least one of an esophageal pressure sampling tube, a thoracic cavity pressure sampling tube, and a carina pressure sampling tube.

In some examples, the pressure sampling tube may comprise the pressure sensor. The pressure sensor may be configured to acquire pressure that reflects the self-respiratory effort of the patient.

In some examples, in step S300, one or more of the speed, trend, and amplitude of the pressure change that reflects the self-respiratory effort are used.

In some examples, in step S300, the amplitude of the pressure change and the trend of the pressure change may be obtained. The amplitude of the pressure change may be a difference value between the measured pressure and end-tidal pressure. During the expiratory phase of the respirator, when the patient is at the end of expiration, the measured pressure is the end-tidal pressure. The end-tidal pressure may be end-tidal pressure of a previous time, or may be an average value of end-tidal pressure of a preset quantity of previous respiratory periods. The end-tidal pressure at the previous time is end-tidal pressure of a previous period of the measured pressure.

Figure 3:
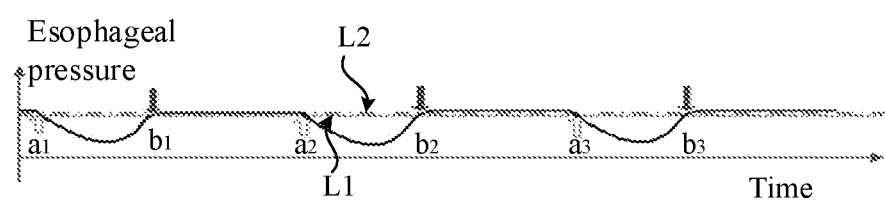
FIG. 3 is a schematic diagram of a waveform of esophageal pressure according to the present disclosure.

In some examples, the amplitude and trend of an esophageal pressure change may be obtained, to reflect the self-respiratory effort of the patient. Specifically, during autonomous inspiration of the patient, because of the contraction of respiratory muscle, the volume of the thoracic cavity increases, and therefore thoracic cavity pressure (esophageal pressure) decreases. When the patient is at the end of inspiration, because the autonomous inspiration of the patient is about to end, the respiratory muscle gradually relaxes, and the thoracic cavity pressure (esophageal pressure) of the patient gradually rises. FIG. 3 is a schematic diagram of a waveform of esophageal pressure according to the present disclosure. FIG. 3 may show the trend of the esophageal pressure change. The amplitude of the esophageal pressure change may be a difference value between the measured esophageal pressure and end-expiratory esophageal pressure.

In some examples, in step S300, the amplitude of the pressure change and the trend of the pressure change may be obtained. The amplitude of the pressure change may be a change amplitude of an actually measured pressure and a predicted pressure, that is, the magnitude of a difference value between the actually measured pressure and the predicted pressure. The predicted pressure may be obtained by performing fitting prediction on the actually measured pressure. The fitting prediction is a process of establishing a model based on at least two sampling points to approximate an actual data sequence.

Figure 4:
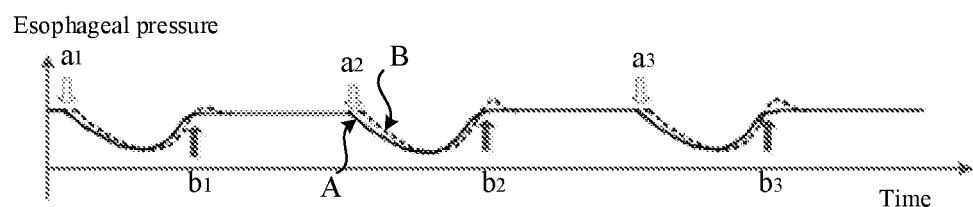
FIG. 4 is a schematic diagram of a waveform of predicted pressure of esophageal pressure according to the present disclosure.

In some examples, the amplitude and trend of the esophageal pressure change may be obtained. FIG. 4 is a schematic diagram of a waveform of predicted pressure of esophageal pressure according to the present disclosure. FIG. 4 may show a relationship between the actually measured pressure and the predicted pressure and the trend of the actually measured pressure. As shown in FIG. 4, a waveform A is actually measured esophageal pressure, and a waveform B is predicted esophageal pressure.

In some other examples, step S300 may obtain the speed of the pressure change. The speed of the pressure change may be the slope of the measured pressure, or may be sometimes referred to as a pressure gradient value.

In some examples, the measured pressure may be a discrete signal. The speed of the pressure change may be acquired by performing differential operation on the obtained pressure. Certainly, the speed of the pressure change may be obtained by performing linear fitting on instantaneous pressure within a preset time to calculate the slope of the instantaneous pressure. The preset time may be 200 ms to 600 ms.

Figure 5:
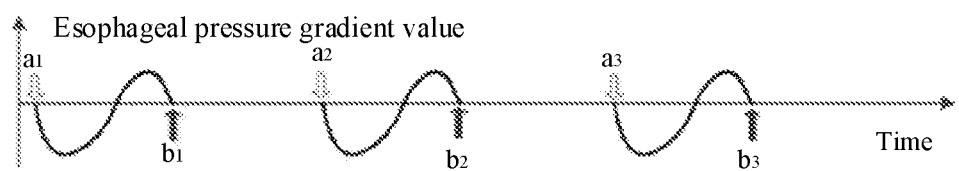
FIG. 5 is a schematic diagram of a slope curve of esophageal pressure shown in FIG. 4.

In some examples, the speed of the esophageal pressure change may be obtained. That is, an esophageal pressure gradient value may be obtained. FIG. 5 is a schematic diagram of a slope curve of esophageal pressure shown in FIG. 4. FIG. 5 may show the speed of the esophageal pressure change.

In some examples, after step S300 of obtaining a pressure waveform that reflects the self-respiratory effort of the patient, an envelope may be extracted from the pressure waveform.

In some examples, an instantaneous root mean square of the pressure waveform is calculated, to obtain the envelope of the pressure waveform.

Figure 6:
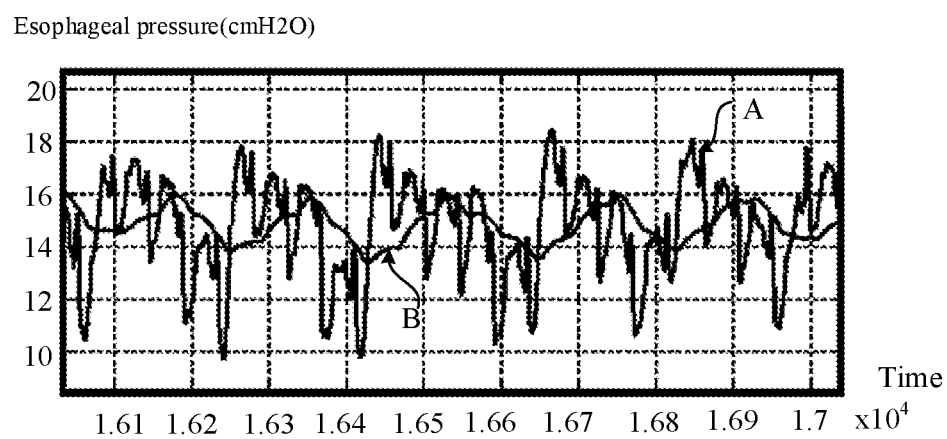
FIG. 6 is a schematic diagram of a waveform of esophageal pressure according to the present disclosure.

In some examples, an esophageal pressure waveform may be obtained. FIG. 6 is a schematic diagram of a waveform of esophageal pressure according to the present disclosure. A curve A in FIG. 6 is the esophageal pressure waveform. Because an acquisition position of esophageal pressure is close to the heart of the patient, for the interference from the vibration of heartbeat, there are many interference signals in the curve A.

In some examples, the ventilation control method for a respirator may further comprise: identifying the inspiratory trigger moment or the expiratory trigger moment of the patient according to the measured pressure change that reflects the self-respiratory effort of the patient (step S400).

In step S400, the measured pressure change may comprise a pressure change in one or more of esophageal pressure, thoracic cavity pressure, intrapulmonary pressure, carina pressure, intragastric pressure or cannula tip pressure of the patient. Therefore, the inspiratory trigger moment or the expiratory trigger moment of the patient can be identified according to the pressure change in one or more of esophageal pressure, thoracic cavity pressure, intrapulmonary pressure, carina pressure, intragastric pressure or cannula tip pressure.

In some examples, in step S400, the inspiratory trigger moment or the expiratory trigger moment may be identified according to one or more of the speed, trend, and amplitude of the pressure change that reflects the self-respiratory effort. In this case, the inspiratory trigger moment or the expiratory trigger moment of the patient is accurately identified.

In step S400, when the pressure change that reflects the self-respiratory effort of the patient is the amplitude and trend of the pressure change, a specific method of step S400 is: identifying, when the pressure change is in a downward trend and the amplitude of the pressure change reaches a first threshold, that the patient is at the inspiratory trigger moment, and identifying, when the pressure change is in an upward trend and the amplitude of the pressure change reaches a second threshold, that the patient is at the expiratory trigger moment. In this case, the inspiratory trigger moment or expiratory trigger moment of the patient can be accurately identified.

In this implementation, the amplitude of the pressure change is a change amplitude of the actually measured pressure and end-tidal pressure. Therefore, in step S400, the inspiratory trigger moment or expiratory trigger moment of the patient is identified according to the change amplitude of the actually measured pressure and the end-tidal pressure and with reference to the trend of the actually measured pressure.

Specifically, in step S400, a first difference value between the actually measured pressure and the end-tidal pressure may be obtained. The size of the first difference value may reflect the amplitude of the actually measured pressure change. Therefore, in step S400, when the actually measured pressure change is in a downward trend and the first difference value reaches the first threshold, it is identified that the patient is at the inspiratory trigger moment, and when the actually measured pressure change is in an upward trend and the first difference value reaches the second threshold, it is identified that the patient is at the expiratory trigger moment.

In some examples, the first threshold and the second threshold both are constant thresholds or variable thresholds. In this case, thresholds can be set or adjusted according to the experience of medical personnel. The constant thresholds are unchangeable thresholds set in the respirator. The variable thresholds are thresholds that are set in the respirator and can be manually changed. In this case, the first threshold and the second threshold may be set or adjusted according to experience of medical personnel. Certainly, the first threshold and the second threshold may be alternatively obtained by the machine through learning of historical data.

In some examples, the actually measured pressure may be esophageal pressure. That is, the amplitude and trend of the esophageal pressure change may be obtained. As shown in FIG. 3, for example, it is specified that an intersection between a line L1 and an esophageal pressure waveform diagram satisfies a condition that the first difference value reaches the first threshold, and an intersection between a line L2 and the esophageal pressure waveform diagram satisfies a condition that the first difference value reaches the second threshold.

In some examples, as shown in FIG. 3, when esophageal pressure is in a downward trend and esophageal pressure decreases to the intersection between the line L1 and the esophageal pressure waveform diagram, the patient is in the inspiratory trigger moment. a1, a2, and a3 in the figure separately reflect inspiratory trigger moments within different periods. The inspiratory trigger moments are not limited to a1, a2, and a3 in FIG. 3. "am" may reflect an inspiratory trigger moment of the respirator within a different respiratory period. "m" may be 1, 2, 3, 4, 5, 6 or the like.

In some examples, as shown in FIG. 3, esophageal pressure is in an upward trend and when esophageal pressure increases to the intersection between the line L2 and the esophageal pressure waveform diagram, the patient is at the expiratory trigger moment. b1, b2, and b3 in the figure separately reflect expiratory trigger moments within different periods. Similar to "am", "bm" may reflect expiratory trigger moments of the respirator within a different respiratory period. "m" may be 1, 2, 3, 4, 5, 6 or the like.

In another implementation, the amplitude of the pressure change is a change amplitude of an actually measured pressure and a predicted pressure, and the change amplitude of the actually measured pressure and the predicted pressure is a difference value between the predicted pressure and the actually measured pressure. Therefore, in step S400, the inspiratory trigger moment or expiratory trigger moment of the patient is identified according to the change amplitude of the actually measured pressure and the predicted pressure and with reference to the trend of the actually measured pressure.

In this implementation, the first threshold and the second threshold are both greater than zero. The first threshold and the second threshold may have different values from the first threshold and the second threshold in the first implementation.

In this implementation, when the first threshold and the second threshold are both greater than zero, it may be understood that the actually measured pressure is less than the predicted pressure. When the difference value between the predicted pressure and the actually measured pressure satisfies the first threshold or the second threshold, it indicates that the difference value between the predicted pressure and the actually measured pressure is greater than zero. That is, the predicted pressure is greater than the actually measured pressure.

Specifically, in step S400, a second difference value between the predicted pressure and the actually measured pressure may be obtained. The value of the second difference value may reflect the change amplitude of the actually measured pressure and the predicted pressure at the same moment. Therefore, in step S400, when the actually measured pressure change is in a downward trend and the second difference value reaches the first threshold, it is identified that the patient is at the inspiratory trigger moment, and when the actually measured pressure change is in an upward trend and the second difference value reaches the second threshold, it is identified that the patient is at the expiratory trigger moment.

In some examples, when the actually measured pressure is in a downward trend, the actually measured pressure is less than the predicted pressure, and the second difference value reaches the first threshold, it is identified that the patient is at the inspiratory trigger moment. When the actually measured pressure is in an upward trend, the predicted pressure is greater than the actually measured pressure, and the second difference value reaches the second threshold, it is identified that the patient is at the expiratory trigger moment. In this case, for the first threshold and the second threshold, a relationship between a threshold and zero is not limited.

The first threshold and the second threshold both are constant thresholds or variable thresholds. Certainly, the first threshold and the second threshold may be alternatively obtained by the machine through learning of historical data.

In some examples, the actually measured pressure may be esophageal pressure. That is, the actually measured pressure and the predicted pressure of esophageal pressure may be obtained, and the amplitude and trend of the esophageal pressure change are obtained. As shown in FIG. 4, the waveform B is the actually measured pressure of esophageal pressure, and the waveform B is the predicted pressure of esophageal pressure.

In some examples, as shown in FIG. 4, when the actually measured pressure of esophageal pressure (the waveform A) is in a downward trend, the actually measured pressure of esophageal pressure is less than the predicted pressure (the waveform B), and the second difference value reaches the first threshold, it is identified that the patient is at the inspiratory trigger moment. When the actually measured pressure of esophageal pressure is in an upward trend, the predicted pressure is greater than the actually measured pressure of esophageal pressure, and the second difference value reaches the second threshold, it is identified that the patient is at the expiratory trigger moment.

The foregoing is two implementations of step S400 based on the amplitude and trend of the pressure change.

In some examples, when the pressure change that reflects the self-respiratory effort of the patient is the speed of the pressure change, a specific method of step S400 is: identifying, when the speed of the pressure change decreases from near zero, that the patient is at the inspiratory trigger moment, and identifying, when the speed of the pressure change decreases to near zero, that the patient is at the expiratory trigger moment. The speed of the pressure change may also be referred to as a pressure gradient value. Therefore, when the pressure gradient value crosses zero and gradually decreases, it is identified that the patient is at the inspiratory trigger moment, and when the pressure gradient value decreases to zero, it is identified that the patient is at the expiratory trigger moment. In this case, the inspiratory trigger moment or expiratory trigger moment of the patient can be accurately identified.

In some examples, the speed of the pressure change may be the slope of the measured pressure.

In some examples, the measured pressure may be a discrete signal. The speed of the pressure change may be acquired by performing differential operation on the obtained pressure.

In some examples, the measured pressure may be continuous pressure signals, and the derivative of the continuous pressure signals is calculated to obtain the slope of the continuous pressure signals. The slope of the continuous pressure signals is equivalent to the speed of the pressure change.

In some examples, the actually measured pressure may be esophageal pressure. That is, the speed of the esophageal pressure change may be obtained. As shown in FIG. 5, FIG. 5 is a curve diagram of the speed of the esophageal pressure change (which is also referred to as an esophageal pressure gradient value).

In step S23, the speed of the esophageal pressure change is compared with the zero to determine a relationship, and a change trend of the speed of the esophageal pressure change is determined, that is, the esophageal pressure gradient value is compared with the zero to determine a relationship, and the change trend of the esophageal pressure gradient value is determined, so that the inspiratory trigger moment or expiratory trigger moment of the patient can be accurately identified.

In some examples, the vertical axis in FIG. 5 reflects the slope of esophageal pressure. That is, the vertical axis reflects the speed of the esophageal pressure change. As shown in FIG. 5, when the esophageal pressure gradient value decreases from near zero, it is identified that the patient is at the inspiratory trigger moment. When the esophageal pressure gradient value decreases to near zero, it is identified that the patient is at the expiratory trigger moment. "am" may reflect the inspiratory trigger moment of the respirator within a different respiratory period. "m" may be 1, 2, 3, 4, 5, 6 or the like. "bm" may reflect the expiratory trigger moment of the respirator within a different respiratory period. "m" may be 1, 2, 3, 4, 5, 6 or the like.

In some examples, for the pressure change, when a pressure waveform that reflects the self-respiratory effort of the patient is obtained and an envelope is extracted from the pressure waveform, a specific method of step S400 is: identifying the inspiratory trigger moment or the expiratory trigger moment of the patient according to the envelope. In this case, the inspiratory trigger moment or expiratory trigger moment of the patient can be accurately identified based on the envelope.

In some examples, a specific method of identifying the inspiratory trigger moment or the expiratory trigger moment of the patient according to the envelope is: identifying the inspiratory trigger moment and the expiratory trigger moment of the patient according to a peak and a trough of the envelope. In this case, the inspiratory trigger moment and the expiratory trigger moment of the patient can be identified based on the peak and the trough of the envelope.

In some examples, when the pressure waveform is at a peak, it is identified that the inspiratory trigger moment of the patient, and when the pressure waveform is at a trough, it is identified that the expiratory trigger moment of the patient.

In some examples, the inspiratory trigger moment does not necessarily correspond to a peak of the pressure waveform, and the moment when the pressure waveform rises or drops to a first set proportion of the peak may be considered as the inspiratory trigger moment, or a first set time at a delay after the moment corresponding to a peak may be considered as the inspiratory trigger moment. Similarly, the expiratory trigger moment does not necessarily correspond to a peak of the pressure waveform, and the moment when the pressure waveform drops or rises to a second set proportion of a trough may be considered as the expiratory trigger moment, or a second set time at a delay after the moment corresponding to a trough may be considered as the expiratory trigger moment.

In some examples, the pressure waveform may comprise an interference signal such as a heartbeat signal. Filtering processing may be performed on the pressure waveform, to filter out the interference signal such as the heartbeat signal.

In some examples, because the frequency of the heartbeat signal in the interference signal is higher than the frequency of respiration, for esophageal pressure, the heartbeat signal is a high frequency interference signal. In this case, low-pass filtering may be performed on an initial waveform to remove a high frequency interference signal such as a heartbeat signal in the initial waveform.

In some examples, the pressure waveform may be an initial waveform of esophageal pressure. As shown in FIG. 6, the waveform A is the initial waveform of esophageal pressure, and the waveform B is a target waveform of esophageal pressure. The target waveform is obtained by extracting the envelope from an initial waveform.

In some examples, as shown in FIG. 6, when the target waveform (the waveform B) of esophageal pressure is at a peak, it is identified that the patient is at the inspiratory trigger moment. When the target waveform is at a trough, it is identified that the patient is at the expiratory trigger moment.

In the present disclosure, the ventilation device is provided to provide ventilation airflow to a patient, the pressure and/or flow velocity of ventilation is monitored, a pressure change that reflects the self-respiratory effort of the patient is measured, and an inspiratory trigger moment or an expiratory trigger moment of the patient is identified according to the pressure change. Therefore, a delay problem that occurs when the inspiratory trigger moment or expiratory trigger moment of the patient is determined according to air passage pressure or air passage flow velocity can be resolved. In addition, the pressure change that reflects the self-respiratory effort of the patient can avoid a leakage problem.

Figure 7:
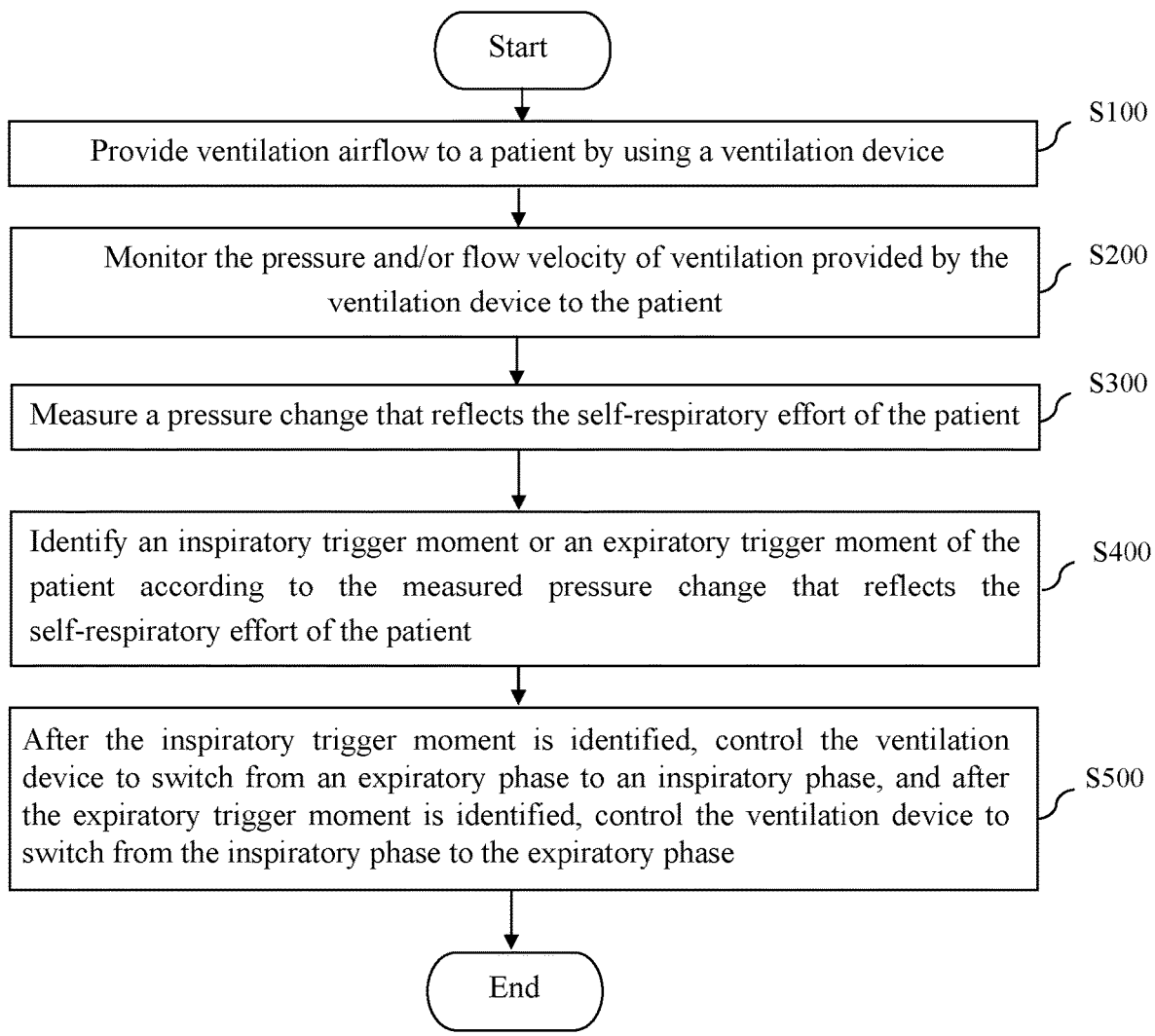
FIG. 7 is a schematic flowchart of another ventilation control method for a respirator according to the present disclosure.

FIG. 7 is a schematic flowchart of another ventilation control method for a respirator according to the present disclosure.

In some examples, as shown in FIG. 7, the ventilation control method for a respirator may further comprise: after the inspiratory trigger moment is identified, controlling the ventilation device to switch from an expiratory phase to an inspiratory phase, and after the expiratory trigger moment is identified, controlling the ventilation device to switch from the inspiratory phase to the expiratory phase (step S500). In this case, expiration or inspiration of the patient can be facilitated.

In some examples, after the inspiratory trigger moment and the expiratory trigger moment are identified, the ventilation control method for a respirator may further comprise: outputting the inspiratory trigger moment and the expiratory trigger moment. In this case, the inspiratory trigger moment and the expiratory trigger moment of the patient can be identified.

In some examples, after the inspiratory trigger moment and the expiratory trigger moment are identified, the ventilation control method for a respirator may further comprise: computing patient-respirator synchronization information. In this case, patient-respirator synchronization of the respirator can be determined.

Figure 8:
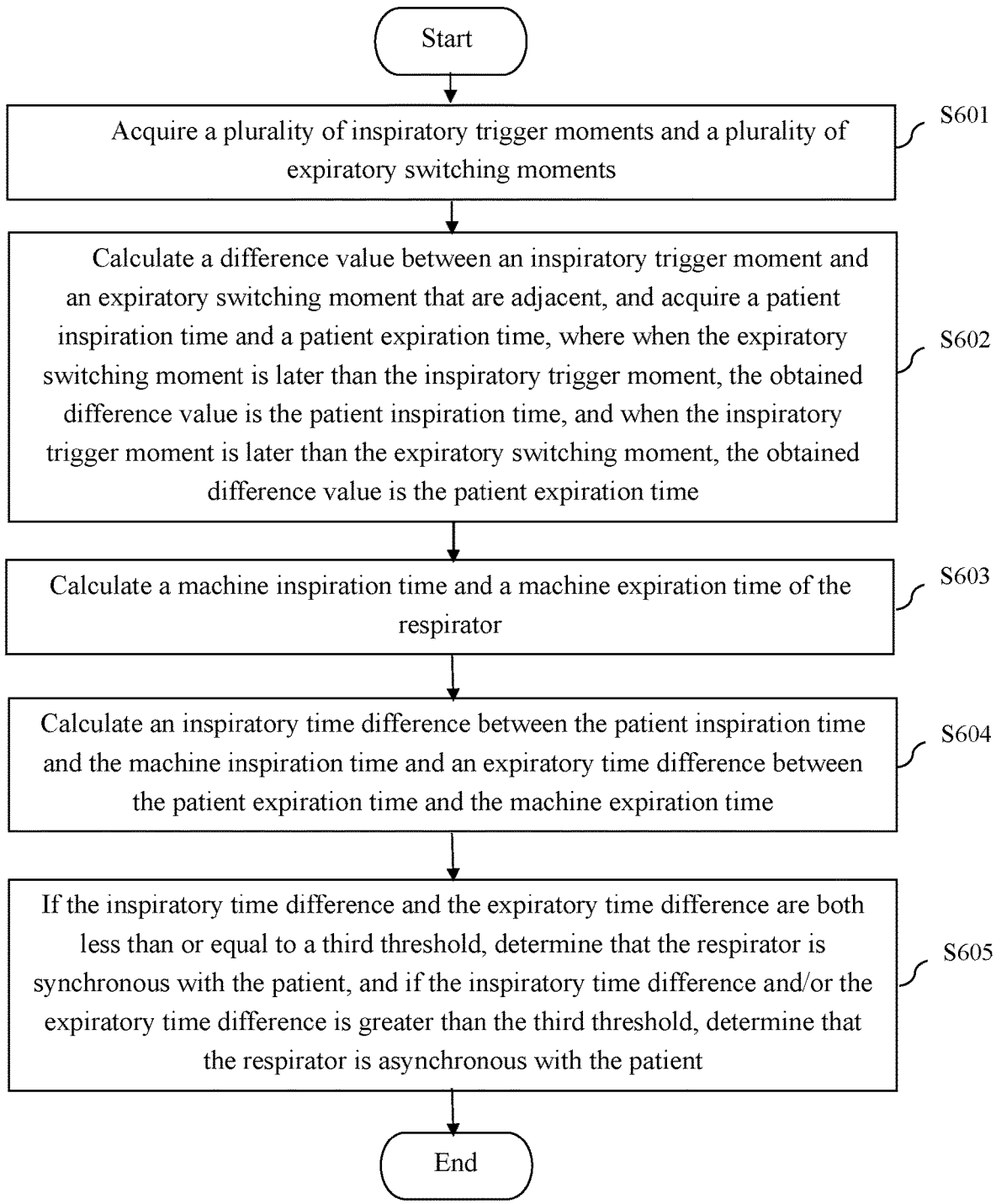
FIG. 8 is a schematic flowchart of a method for determining patient-respirator synchronization of a respirator according to an embodiment of the present disclosure.

FIG. 8 is a schematic flowchart of a method for determining patient-respirator synchronization of a respirator according to an embodiment of the present disclosure.

In some examples, as shown in FIG. 8, the method for determining patient-respirator synchronization of a respirator comprises: acquiring a plurality of inspiratory trigger moments and a plurality of expiratory trigger moments (step S601).

In step S601, a respirator uses the foregoing ventilation control method to acquire moments corresponding to switching. These moments comprise an inspiratory trigger moment (see a1 in FIG. 3) and an expiratory trigger moment (see b1 in FIG. 3).

Because a patient keeps breathing, the respirator keeps switching between the inspiratory phase and the expiratory phase. Therefore, a plurality of inspiratory trigger moments "am" (for example, a1) and a plurality of expiratory trigger moments "bm" (for example, b1) alternate with each other. FIG. 3 schematically shows a limited quantity of inspiratory trigger moments and expiratory trigger moments. However, the inspiratory trigger moment "am" and the expiratory trigger moment "bm" of the present disclosure are not limited to the quantities in FIG. 3.

In some examples, as shown in FIG. 8, the method for determining patient-respirator synchronization of a respirator may further comprise: calculating a difference value between an inspiratory trigger moment and an expiratory trigger moment that are adjacent, and acquiring a patient inspiration time and a patient expiration time, where when the expiratory trigger moment is later than the inspiratory trigger moment, the obtained difference value is the patient inspiration time, and when the inspiratory trigger moment is later than the expiratory trigger moment, the obtained difference value is the patient expiration time (step S602).

In step S602, because the inspiratory trigger moments and expiratory trigger moments alternate with each other in step S601 and the patient is in an inspiratory stage or an expiratory stage between the inspiratory trigger moment and the expiratory trigger moment, the difference value between an inspiratory trigger moment and an expiratory trigger moment that are adjacent is calculated, and the patient inspiration time and the patient expiration time can be acquired.

In step S602, the inspiratory trigger moment and the expiratory trigger moment used to calculate the difference value are compared. If the inspiratory trigger moment is earlier than the expiratory trigger moment, it represents that the patient enters the inspiratory stage at the inspiratory trigger moment, and ends inspiration at the expiratory trigger moment. Therefore, the obtained difference value is the patient inspiration time. If the expiratory trigger moment is earlier than the inspiratory trigger moment, it represents that the patient enters the expiratory stage at the expiratory trigger moment, and ends inspiration at the inspiratory trigger moment. Therefore, the obtained difference value is the patient expiration time.

In some examples, as shown in FIG. 8, the method for determining patient-respirator synchronization of a respirator may further comprise: calculating a machine inspiration time and a machine expiration time of the respirator (step S603).

In step S603, the air pressure or gas flow velocity in a ventilation device 10 changes during machine inspiration and machine expiration of the respirator, and the machine inspiration time and the machine expiration time of the respirator are recorded according to a change in the air pressure or gas flow velocity.

In some examples, as shown in FIG. 8, the method for determining patient-respirator synchronization of a respirator may further comprise: calculating an inspiratory time difference between the patient inspiration time and the machine inspiration time and an expiratory time difference between the patient expiration time and the machine expiration time (step S604).

In some examples, as shown in FIG. 8, the method for determining patient-respirator synchronization of a respirator may further comprise: if the inspiratory time difference and the expiratory time difference both are less than or equal to a third threshold, determining that the respirator is synchronous with the patient, and if the inspiratory time difference and/or the expiratory time difference is greater than the third threshold, determining that the respirator is asynchronous with the patient (step S605).

In step S605, the third threshold may be a threshold set by medical personnel according to experience. The time of the third threshold usually represents a maximum tolerable error time of the patient when patient-respirator conflict does not occur. If the inspiratory time difference and the expiratory time difference both are less than or equal to the third threshold, a respiratory period of the respirator is basically synchronous with a respiratory period of the patient, that is, the respirator is synchronous with the patient. If at least one of the inspiratory time difference and the expiratory time difference is greater than the third threshold, the respirator is not synchronous with the patient.

In addition, in some examples, an inspiratory phase start moment and an expiratory phase start moment of the respirator are recorded. The inspiratory trigger moment of the patient is compared with the inspiratory phase start moment of the respirator to obtain an advance time or a delay time of the respirator entering the inspiratory phase relative to the patient. The expiratory trigger moment of the patient may be compared with the expiratory phase start moment, to obtain an advance time or a delay time of the respirator entering the expiratory phase relative to the patient.

In an implementation, the synchronization information obtained by using the foregoing method for determining patient-respirator synchronization may be a time difference between the inspiratory trigger moment (or the expiratory trigger moment) of the patient and the inspiratory trigger moment (or the expiratory trigger moment) of the respirator.

In an implementation, the synchronization information obtained by using the foregoing method for determining patient-respirator synchronization may be a time difference between the inspiration time (or the expiration time) of the patient and the machine inspiration time (the machine expiration time) of the respirator.

This implementation is not limited thereto. The synchronization information obtained by using the foregoing method for determining patient-respirator synchronization may be a ratio of the time difference to the respiratory period or the like. The respiratory period may further be replaced with an inspiratory period or an expiratory period.

In addition, in some examples, the pressure change may further be used to determine the position of a sampling tube for measuring pressure. For example, a pressure waveform obtained by the second monitor 30 is observed on the display module. Because the waveform may reflect a respiratory rhythm of the patient. If a respiratory rhythm of the observed waveform is unstable, it indicates that the position of a sampling tube is incorrectly placed or the patient cannot breathe normally. In this case, an alarm device works to remind medical personnel.

In some embodiments, a plurality of manners may be used to indicate that the respiratory rhythm is unstable. For example, peak and trough values of a waveform do not have a pattern, the frequency of a waveform is unstable, and a difference value between peak and trough values is less than a preset threshold. The preset threshold may be a difference value between peak and trough values of a measured pressure waveform when the patient breathes normally.

Figure 9A:
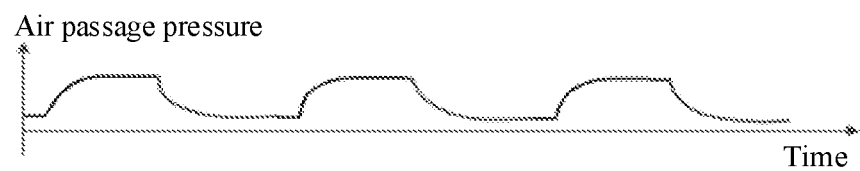
FIG. 9a is a schematic diagram of a waveform of air passage pressure according to the present disclosure.
Figure 9B:
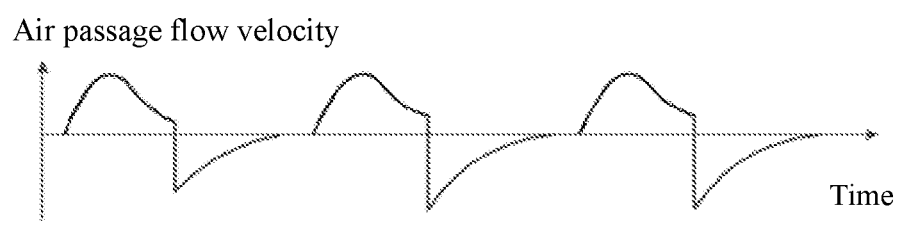
FIG. 9b is a schematic diagram of a waveform of air passage flow velocity according to the present disclosure.

FIG. 9a is a schematic diagram of a waveform of air passage pressure according to the present disclosure. FIG. 9b is a schematic diagram of a waveform of air passage flow velocity according to the present disclosure.

In some examples, the ventilation control method for a respirator may further comprise measuring air passage pressure and/or air passage flow velocity. As shown in FIG. 9a or FIG. 9b, when the air passage pressure is in a downward trend and/or the air passage flow velocity is in an upward trend, it is identified that the patient is at the inspiratory trigger moment, and when the air passage pressure is in an upward trend and/or the air passage flow velocity is in a downward trend, it is identified that the patient is at the expiratory trigger moment. In addition, in the ventilation control method for a respirator, the air pressure and/or flow velocity in the inspiratory phase and the expiratory phase may further be controlled according to the air passage pressure and/or air passage flow velocity target. The air passage pressure and/or air passage flow velocity target may be a preset pressure value or flow velocity value.

In some examples, the ventilation control method for a respirator may further measure both air passage pressure and/or air passage flow velocity and the pressure change that reflects the self-respiratory effort of the patient. The inspiratory trigger moment or the expiratory trigger moment of the patient is identified by determining the air passage pressure and/or air passage flow velocity and determining the pressure change that reflects the self-respiratory effort of the patient, to make ventilation switching of the respirator 1 more accurate.

In addition, the foregoing ventilation control method according to the esophageal pressure change may represent a ventilation control method based on the pressure change. For example, the waveform of thoracic cavity pressure is basically the same as esophageal pressure. Therefore, for the ventilation control method based on thoracic cavity pressure, reference may be made to the ventilation control method based on esophageal pressure. In addition, although there is a difference between the waveform of carina pressure and the waveform of esophageal pressure, in terms of method, the ventilation control method based on carina pressure is similar to the ventilation control method based on esophageal pressure. Therefore, for the ventilation control method based on carina pressure, reference may be made to the ventilation control method based on esophageal pressure. In this case, the ventilation control method based on esophageal pressure in the foregoing implementations may be considered as the ventilation control method based on the measured pressure. Certainly, for intrapulmonary pressure, intragastric pressure or cannula tip pressure, reference may be made to the ventilation control method based on esophageal pressure.

The embodiments of the present disclosure are described above in the specific implementations. Although the foregoing embodiments are directly described in these descriptions, it should be understood that a person skilled in the art may conceive of changes and/or variations to the specific embodiments shown and described herein. Any such changes or variations that fall within the scope of the description are also intended to be covered therein. Unless specially indicated, the intention of the inventor is that the words and expressions in the descriptions and claims are endowed with meanings that are common and conventional to a person skilled in the art.

In addition, in some embodiments, numerical parameters described in the descriptions and appended claims are approximate values, and may be changed according to expected characteristics to be obtained in specific embodiments. In some embodiments, the numerical parameters should be explained according to a quantity of reported effective numbers and by applying conventional rounding technology. Although wide value ranges and parameters described in some embodiments of the present disclosure are approximate values, the numerical values described in specific examples are reported as precisely as possible. The numerical values presented in some embodiments of the present disclosure may include some errors caused by standard deviations that are definitely found in corresponding tests and measurements. Various aspects of the subject described herein may be used separately or may be used in combination with any one or more of other aspects described in the present disclosure.

The invention claimed is:

1. A respirator, comprising:
   a ventilation device, configured for providing a ventilation airflow to a patient;
   a monitor, configured for measuring a pressure change at a body muscle of the patient other than an air passage of the patient that reflects a self-respiratory effort of the patient and measuring a pressure waveform that reflects the self-respiratory effort of the patient using a pressure sensor; and
   a processor, configured for identifying an inspiratory trigger moment and an expiratory trigger moment of the patient according to the pressure change at the body muscle of the patient other than the air passage of the patient that reflects the self-respiratory effort of the patient, wherein the inspiratory trigger moment is a first time point in a timeline where a first expiratory phase is switched to an inspiratory phase, and the expiratory trigger moment is a second time point in the timeline where the inspiratory phase is switch to a second expiratory phase,
   wherein the processor is further configured for:
   controlling the ventilation device to switch from the first expiratory phase to the inspiratory phase, when the second expiratory trigger moment is identified;
   controlling the ventilation device to switch from the inspiratory phase to the expiratory phase, when the expiratory trigger moment is identified;
   extracting an envelope from the pressure waveform that reflects the self-respiratory effort of the patient;
   determining a peak and a trough of the envelope; and
   identifying the inspiratory trigger moment of the patient as the moment when the envelope is at the peak and identifying the expiratory trigger moment of the patient as the moment when the envelope is at the trough.

2. The respirator of claim 1, wherein
   the pressure change comprises one or more of an esophageal pressure change or an intragastric pressure change.

3. The respirator of claim 1, wherein the processor is further configured for
outputting the inspiratory trigger moment and the expiratory trigger moment to a display module, after the inspiratory trigger moment and the expiratory trigger moment are identified.

4. The respirator of claim 1, wherein the processor is further configured for computing patient-respirator synchronization information, after the inspiratory trigger moment and the expiratory trigger moment are identified.

5. The respirator of claim 1, wherein the processor is configured for determining a single peak and a single trough of the envelope for each inspiration phase and each expiration phase.

6. The respirator of claim 1, wherein the processor is configured for:
acquiring a plurality of inspiratory trigger moments and a plurality of expiratory trigger moments;
calculating a difference value between an inspiratory trigger moment and an expiratory trigger moment that are adjacent in the timeline, and acquiring a patient inspiration time and a patient expiration time, wherein when the expiratory trigger moment is later than the inspiratory trigger moment, the calculated difference value is the patient inspiration time, and when the inspiratory trigger moment is later than the expiratory trigger moment, the calculated difference value is the patient expiration time;
calculating a machine inspiration time and a machine expiration time of the respirator;
calculating an inspiratory time difference between the patient inspiration time and the machine inspiration time and an expiratory time difference between the patient expiration time and the machine expiration time; and
when the inspiratory time difference and the expiratory time difference both are less than or equal to a threshold, determining that the respirator is synchronous with the patient; and when at least one of the inspiratory time difference or the expiratory time difference is greater than the threshold, determining that the respirator is asynchronous with the patient.

7. A ventilation control method for a respirator, comprising:
providing a ventilation airflow to a patient by using a ventilation device;
measuring a pressure or a flow velocity of the ventilation airflow provided by the ventilation device to the patient using a pressure sensor or a flow sensor, respectively;
measuring a pressure change at a body muscle of the patient other than an air passage of the patient that reflects a self-respiratory effort of the patient;
measuring a pressure waveform that reflects the self-respiratory effort of the patient according to the measured pressure change using the pressure sensor;
controlling the ventilation device to switch from a first expiratory phase to an inspiratory phase, when an inspiratory trigger moment of the patient is identified;
controlling the ventilation device to switch from the inspiratory phase to a second expiratory phase, when an expiratory trigger moment of the patient is identified;
extracting an envelope from the pressure waveform that reflects the self-respiratory effort of the patient;
determining a peak and a trough of the envelope; and
identifying the inspiratory trigger moment of the patient as the moment when the envelope is at the peak and identifying an expiratory trigger moment of the patient as the moment when the envelope is at the trough, wherein the inspiratory trigger moment is a first time point in a timeline where the first expiratory phase is switched to the inspiratory phase, and the expiratory trigger moment is a second time point in the timeline where the inspiratory phase is switched to the second expiratory phase.

8. The ventilation control method of claim 7, wherein the pressure change comprises one or more of an esophageal pressure change or an intragastric pressure change.

9. The ventilation control method of claim 7, wherein after the inspiratory trigger moment and the expiratory trigger moment are identified, the ventilation control method further comprises:
outputting the inspiratory trigger moment and the expiratory trigger moment to a display module.

10. The ventilation control method of claim 7, wherein after the inspiratory trigger moment and the expiratory trigger moment are identified, the ventilation control method further comprises:
computing patient-respirator synchronization information.

* * * * *